(12) United States Patent
Hollstien et al.

(10) Patent No.: US 7,029,478 B2
(45) Date of Patent: Apr. 18, 2006

(54) METHOD AND APPARATUS FOR DISTAL TARGETING OF LOCKING SCREWS IN INTRAMEDULLARY NAILS

(75) Inventors: David Stuart Hollstien, Templeton, CA (US); Roy B. Hollstien, Atascadero, CA (US)

(73) Assignee: DePuy Products, Inc., Warsaw, IN (US)

( * ) Notice: Subject to any disclaimer, the term of this patent is extended or adjusted under 35 U.S.C. 154(b) by 241 days.

(21) Appl. No.: 10/674,760

(22) Filed: Sep. 30, 2003

(65) Prior Publication Data

US 2005/0070916 A1   Mar. 31, 2005

(51) Int. Cl.
   *A61B 17/58* (2006.01)
(52) U.S. Cl. ...................................... 606/96
(58) Field of Classification Search .................. 606/96, 606/97, 98, 62, 64
   See application file for complete search history.

(56) References Cited

U.S. PATENT DOCUMENTS

| 4,314,251 | A | 2/1982 | Rabb |
| 4,396,885 | A | 8/1983 | Constant |
| 4,621,628 | A | 11/1986 | Brudermann |
| 4,667,664 | A | 5/1987 | Taylor et al. |
| 4,848,327 | A | 7/1989 | Perdue |
| 5,013,317 | A | 5/1991 | Cole et al. |
| 5,049,151 | A | 9/1991 | Durham et al. |
| 5,127,913 | A | 7/1992 | Thomas, Jr. |
| 5,281,224 | A | 1/1994 | Faccioli et al. |
| 5,411,503 | A | 5/1995 | Hollstien et al. |
| 5,433,720 | A | 7/1995 | Faccioli et al. |
| 5,478,343 | A | 12/1995 | Ritter |
| 5,584,838 | A | 12/1996 | Rona et al. |
| 5,707,375 | A * | 1/1998 | Durham et al. ............... 606/96 |
| 5,748,767 | A | 5/1998 | Raab |
| 6,074,394 | A * | 6/2000 | Krause ......................... 606/96 |
| 6,162,228 | A * | 12/2000 | Durham ........................ 606/96 |
| 6,616,670 | B1 | 9/2003 | Simon et al. |

FOREIGN PATENT DOCUMENTS

| EP | 523905 A2 * | 1/1993 |
| EP | 1 358 852 A1 | 11/2003 |
| WO | WO 9302626 A1 * | 2/1993 |

* cited by examiner

*Primary Examiner*—Eduardo C. Robert
*Assistant Examiner*—Jessica R. Baxter
(74) *Attorney, Agent, or Firm*—Maginot, Moore & Beck

(57) ABSTRACT

A system that enables axis-to-axis targeting of an instrument placed within a drill bushing includes a computer, a probe, and a pair of sensor planes mounted to a drill bushing so the planes are perpendicular to one another. The probe has two drive coils that may be mounted near its distal end. The two coils are placed close to one another and are oriented so that when they are selectively coupled to an alternating current source they generate magnetic fields that are orthogonal to one another. The computer receives electrical signals from the sensors in the sensor planes and computes target position, bushing alignment, and bushing orientation values. These values may be presented on a display associated with the computer or used to illuminate directional arrows associated with the drill bushing.

31 Claims, 7 Drawing Sheets

METHOD AND APPARATUS FOR DISTAL TARGETING OF LOCKING SCREWS IN INTRAMEDULLARY NAILS

FIELD OF THE INVENTION

The present invention relates generally to systems for aligning locking screws with openings in intramedullary nails, and more particularly, to such systems that electromagnetically align the locking screws with a transverse opening in an intramedullary nail.

BACKGROUND OF THE INVENTION

Systems for aligning locking screws in intramedullary nails that have been used to secure fractured bones together are known. A description of a number of such systems is set forth in U.S. Pat. No. 5,411,503, which is expressly incorporated herein in its entirety. These systems may be broadly categorized into three classes: x-ray imaging systems, mechanical systems, and electromagnetic systems. X-ray imaging systems use x-ray imaging to provide an image of the limb being treated with the inserted intramedullary nail so the surgeon may view the transverse hole located in the nail. This image facilitates the surgeon's locating the proper position on the external surface of the bone for drilling and aligning the drill bit with the transverse hole. Once the correct drill position and alignment are determined, the x-ray imaging system is removed so the surgeon may then drill a hole through the bone that passes through the hole in the nail. These x-ray imaging systems expose the patient and the surgeon to x-rays and the accumulation of x-rays, especially for the surgeon, may have long term consequences.

The mechanical systems require reference points so the offset distance from the reference point that may be externally determined and viewed by the surgeon correlates to a position that corresponds to the opening of the hole in the intramedullary nail. However, these mechanical systems cannot consistently identify the position and angular orientation of the drill so that the drill bit passes through the transverse hole without engaging the walls of the hole.

Systems that have previously used electromagnetic components for aligning a drill for boring a hole in a bone so the drill bit passes through the transverse hole suffer from a number of limitations. Some systems of this type require that a magnetic dipole be mechanically located within the transverse hole so a magnet dipole on the bone surface aligns with the dipole within the nail. This position may then be marked for drilling, but the angular orientation of the drill must be maintained by the surgeon without further reference to the external dipole that was removed for the drilling operation. Other electromagnetic systems, such as the one disclosed in U.S. Pat. No. 5,584,838, use one or more electromagnetic drive coils and a plurality of electromagnetic flux sensors to guide alignment of a drill bushing with the transverse hole in an intramedullary nail. These systems measure the current or voltage induced in coil sensors associated with a drill bushing by a drive coil that is located within a medullary canal to determine the alignment of the drill bushing axis with the axis of the transverse hole. One limitation of the system disclosed in U.S. Pat. No. 5,584,838 is that the drive coil must be removed from its location within the transverse hole so that the drilling operation may be performed without boring through the drive coil. When the drive coil is removed from the transverse hole the coil sensors no longer generate signals that may be used to align the drill bushing. Consequently, the surgeon must maintain the proper orientation and placement of the drill without any indicia to confirm correct placement of the drill.

One electromagnetic system that overcomes these problems is the system disclosed in U.S. Pat. No. 5,411,503. That system uses a pair of drive coils that are mounted within a probe that is placed within an intramedullary nail after the nail is inserted in the medullary canal of a fractured bone. Two sensor planes mounted in orthogonal relationship to one another are located in fixed relationship with a drill bushing. The drive coils are separated by a distance that corresponds to the offset of the sensor planes from the axis of the drill bushing. The drive coils are oriented so the magnetic fields emitted by the coils are aligned in the same direction but the coils are independently controlled so the field from one of the drive coils does not cut a sensor coil when a magnetic field is being generated by the other drive coil. When the sensor coil planes are aligned with the drive coils so that neither coil induces a current in a sensor coil, the drill bushing is aligned with the transverse hole. The fixed displacement of the sensor planes from the drill bushing is set to place the drill bushing axis in alignment with the transverse hole when no signal is induced in any sensor coil. The forward drive coil is placed very nearly at the transverse hole by engaging a probe stop at the outboard end of the probe with the intramedullary nail when the probe is inserted within the nail.

While the system of U.S. Pat. No. 5,411,503 works well for aligning the axis of a drill bushing with a transverse hole in an intramedullary nail, it suffers from some limitations. For one, aligning a drill bushing axis with a transverse hole so the drill bit enters the hole and passes through the hole without engaging the wall of the hole requires constraining the orientation of the drill bushing so it passes through two points, namely, the entrance and exit openings of the hole. In some applications, a single point, usually the exit point, is all that is required. For example, a surgeon may be able to view one side of a bone and select the position where drilling should begin but be unable to orient the drill bit accurately so it exits the bone at the desired point on the other side of the bone. What is needed is a way of assisting a surgeon in aligning a drill so the drill bit bores through the bone to the exit point as quickly, accurately, and simply as possible.

The system disclosed in U.S. Pat. No. 5,411,503 also requires that the probe and guide are connected to the display via cables. These cables must be sterile since they may come into contact with the blood and bodily fluids from the patient. Additionally, many pieces of equipment in operating rooms have cables and tubes extending from them. Consequently, care must be taken to keep the cables from surgical targeting systems, such as the one disclosed in U.S. Pat. No. 5,411,503, from becoming entangled with the cables and tubes associated with other equipment in the operating room. What is needed is a system that avoids the need for sterilized cables and that reduces the likelihood of cable entanglement.

Another limitation of the system disclosed in U.S. Pat. No. 5,411,503 is a structural weakness introduced into the probe by the placement of the drive coils at the distal end of the probe. The probe is comprised of a main conduit to which the drive coils are mounted at one end and then the main conduit/drive coil assembly is enclosed within a sheath. The drive coils are formed into an integral unit to facilitate probe assembly. The integral unit is formed by orienting the drive coils in the same direction and placing a conduit section of about 1.25 inches in length between the drive coils to stiffen the integral unit. The drive coils and short conduit section are then encapsulated in a polymeric resin with the wires to the drive coils extending in the same direction beyond one end of the drive coil unit. This integral unit is joined by adhesives or the like to the distal end of the conduit with the wires of the integral unit extending down the length of the main conduit. The conduit/integral unit assembly is enclosed within a sheath to form the probe. This probe construction had a structural weakness where the integral unit joined the main conduit. Occasionally, stress on the probe would cause the integral unit to separate from the main conduit at the point where they were joined to one another. What is needed is a way of constructing a drive coil probe that simplifies probe assembly and reduces the likelihood of structural weakness in a probe at a drive coil.

SUMMARY OF THE INVENTION

The present invention addresses the above needs, as well as others, with a probe having an elongated member and a first and a second drive coil mounted to the elongated member, the first and the second drive coils being proximate one another and being oriented so that a magnetic field generated by the first drive coil is orthogonal to a magnetic field generated by the second drive coil. The drive coils are place proximate to one another so that the origin of the magnetic fields emitted by the drive coils appear to be the same from a sensor associated with a surgeon's drill. Preferably, the drive coils are separated by a distance of approximately 0.100 inches or less. This close proximity permits the integral unit containing the two drive coils to be constructed by orienting the drive coils in perpendicular arrangement in close proximity to one another and then encapsulating them in the polymeric resin. This construction simplifies the formation of the integral unit because the short conduit section is no longer required to stiffen the integral unit. Furthermore, greater stress is required at the junction of the integral unit and main conduit before the integral unit is separated from the main conduit. Thus, probe construction is simplified and the probe has greater mechanical strength.

The probe of the present invention preferably uses magnetic dipoles for the drive coils. One magnetic dipole is mounted to the elongated member so that the dipole is horizontally transverse to the longitudinal axis of the elongated member and the second dipole is mounted to the probe so that the dipole is vertically transverse to the longitudinal axis. The drive coils are preferably mounted at the distal end of the elongated member.

The probe of the present invention may be used in a system to locate a target point for a drill bushing. The system is comprised of a probe having two drive coils, the drive coils being mounted proximate to one another in the probe and oriented so that a magnetic field produced by the first drive coil in response to an alternating current is orthogonal to a magnetic field produced by the second drive coil in response to an alternating current, a guide having a pair of sensor planes mounted proximate a drill bushing, the sensor planes being mounted orthogonal to one another, each sensor plane containing a pair of sensors, each sensor generating an electrical signal in response to the magnetic fields produced by the first and second drive coils, and a computer coupled to the sensors in each sensor plane to receive readings from each sensor and to determine the target point of the drill bushing to which the pair of sensor planes is mounted. The sensors in the sensor planes may be inductive coil sensors, Hall effect sensors, magnetoresistive sensors, or other sensors that generate an electrical signal in response to the presence of a magnetic field. The computer may also compute the alignment of the drill bushing with an axis of an intramedullary nail hole that is proximate one of the drive coils. The computer may also generate indicia for indicating the target point of the drill bushing in the plane of one of the drive coils, indicia indicating alignment of the drill bushing with an axis for an intramedullary nail hole that is proximate one of the drive coils, and indicia indicating angular orientation of the drill bushing to an intramedullary nail hole proximate one of the drive coils. These indicia may be displayed by directional indicators associated with the computer or the guide.

In one embodiment of the present invention, the alternating current used to produce the magnetic fields has a frequency in the range of about 20 KHz to 30 KHz, although other frequencies may be used. Generation of the orthogonal magnetic fields may be time multiplexed by selectively coupling only one of the drive coils to the alternating current to generate a magnetic field and then reading an electrical signal from each of the sensors in the sensor planes. Then, the alternating current is decoupled from the active drive coil and coupled to the other drive coil in the probe. The computer obtains a reading of an electrical signal from each of the sensors. The alternating current source is decoupled from the active drive coil and re-coupled to the inactive drive coil so the process may be repeated. In this manner, the alternating current source is maintained at a single frequency and applied to the two drive coils in an alternating manner so the magnetic fields produced by the drive coils do not exist at the same time. The measurements obtained by the computer from the sensors under the effects of first one magnetic field and then the other magnetic field are used to compute a target point, an axis alignment, and a guide rotation. The equations used for this computation require identification of the drive coil to which the alternating current is being supplied, as discussed more fully below. This active drive coil identification may either be supplied by the computer to the probe or by the probe to computer. Preferably, in the time multiplexed mode of operation, the active drive coil identification data is provided by the computer to the probe.

Preferably, generation of the magnetic fields with the drive coils is done in a frequency multiplexed manner. This type of field generation is performed with two alternating current frequencies that are applied simultaneously to the two coils so that the alternating currents at the coils are synchronized. The two currents are applied to the drive coils for a period of time, called a burst, and then decoupled from the drive coils or turned off for a short period. To obtain measurements from the sensor coils, the product of a signal received from each sensor and a first reference signal that corresponds to one of the alternating frequencies is averaged over the period of the burst. A phase locked loop is used to synchronize the quadrature signal for a first reference signal to a signal received from one of the sensors. Multiplication of a sensor signal with the in-phase reference signal effectively demodulates the signal from a sensor coil to provide a signal proportional to the response of a sensor to the magnetic field generated by the drive coil coupled to the alternating current having a frequency corresponding to the reference signal. The sensor coil responses to the magnetic field generated from the first alternating current frequency are measured and provided to the computer where they are stored during a sample interval. To obtain responses to the second magnetic field from the sensor coils, the product of each sensor signal and a second in-phase reference signal that corresponds to the other alternating current frequency is averaged. A signal from the phase locked loop is used to keep the second reference signal in phase with the sensor responses to the second magnetic field. The signal from the phase locked loop may be used to synchronize both reference signals because the alternating signals at the drive coils are synchronized. The sensor coil responses to the magnetic field generated from the second alternating current frequency are also measured and sent to the computer where they are stored during the sample interval. Thus, a signal from a sensor may be measured for its response to both magnetic fields contemporaneously.

The values obtained for a sensor over the sample interval may be averaged to statistically smooth the data. The sample interval also may be sized to reduce possible interference from magnetic fields generated from power mains in a facility. Preferably, the sample interval is a sub-multiple of the period of the power mains frequency, which preferably is 0.10 seconds for power mains supplying current at 50 Hz or 60 Hz range. By averaging sensor readings over a 0.10 second period, the effect of interference due to power mains is minimized. Thus, the system may be used in areas of the world where either power frequency is used without the need to change the sample interval. The computer may then use the averaged coil sensor values to compute the target position, axis alignment, and guide orientation.

Although the sensor readings may be provided to the computer for computation of positional data, the readings are preferably provided to the computer in a wireless manner. That is, the guide and the computer include a transceiver for wireless communication. Preferably, the transceiver conforms to the Bluetooth standard. As a result, the system of the present invention may be implemented without requiring sterilized cables and, thus, reducing the likelihood of cable entanglement in the operating room.

The computer includes a program that calculates parameters from equations regarding magnetic flux at a point in a field. These equations, discussed more fully below, are appropriate to describe the signals generated by the sensors in the sensor planes because the distance of a sensor from the drive coils is substantially greater than the size of the magnetic dipoles or other magnetic field generators used as drive coils. The equations and the measurements of the electrical signals generated by the sensors in the sensor planes may be used by the computer to determine a target point, transverse hole axis alignment, and drill bushing angular orientation.

In another embodiment of the present invention, the drive coils may be mounted or embedded in a thimble or glove comprised of elastic material. The drive coils are located proximate to one another and, preferably, at a distance of about 0.100 inches or less. The closeness of the drive coils enables the coils to be incorporated in a thimble or glove that may be worn by a surgeon using the system described above. The surgeon wearing the thimble or glove may place the thimble or glove portion containing the drive coils at a point on a bone that is opposed to a point of entry that may be viewed by the surgeon. The surgeon may then place the drill bushing on the point of entry and observe the target point indicia generated by the computer. By adjusting the angular orientation of the drill bushing, the surgeon may observe the movement of the target point until it corresponds to the origin of the magnetic fields at the drive coils in the thimble or glove. The surgeon may then commence drilling and continue to observe the indicia to facilitate holding the drill on the target point at the origin until the drilling operation is completed.

The above described features and advantages, as well as others, will become more readily apparent to those of ordinary skill in the art by reference to the following detailed description and accompanying drawings.

DETAILED DESCRIPTION

Figure 1:
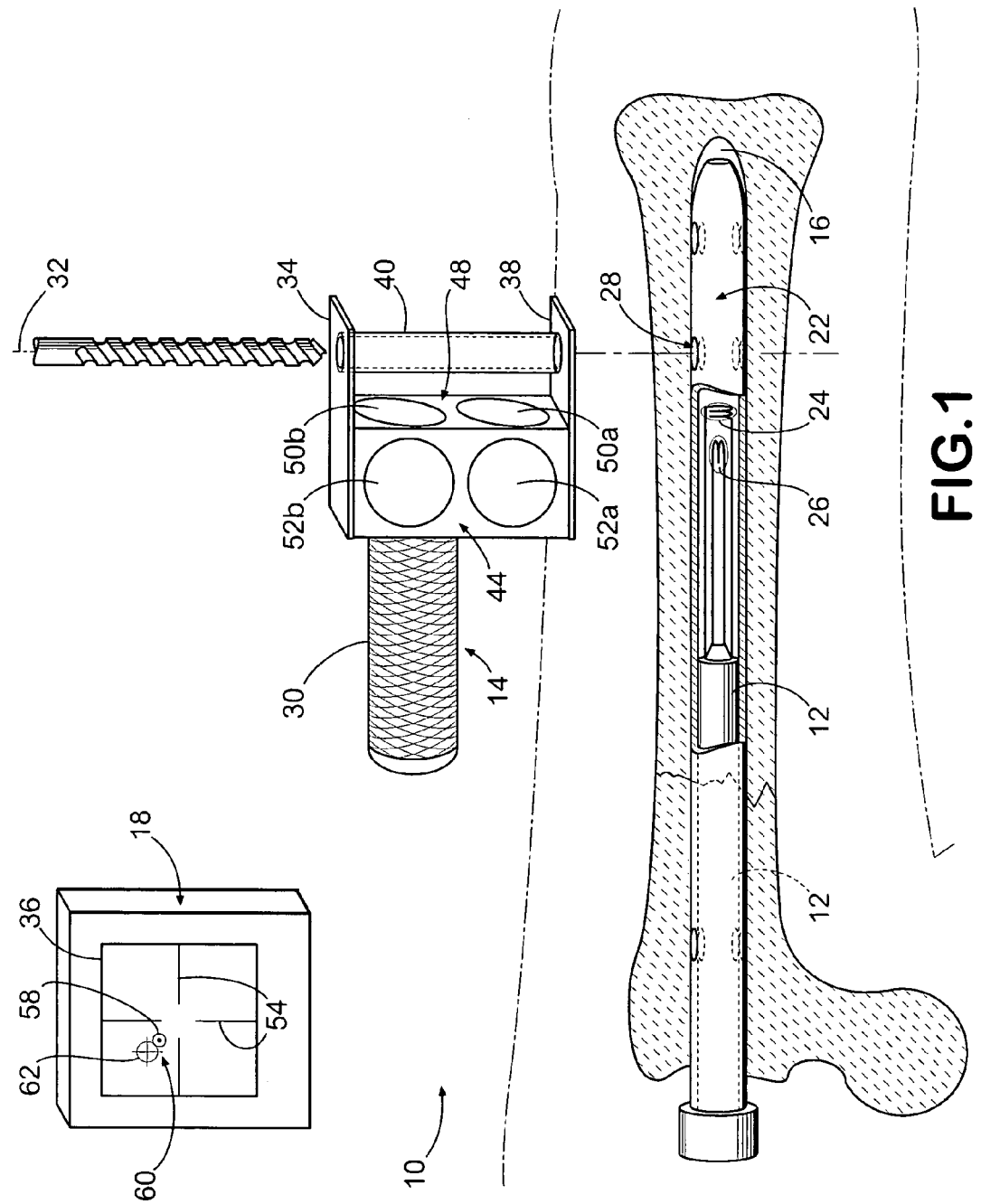
FIG. 1 is a depiction of a system made in accordance with the principles of the present invention to perform axis-to-axis targeting.
Figure 2:
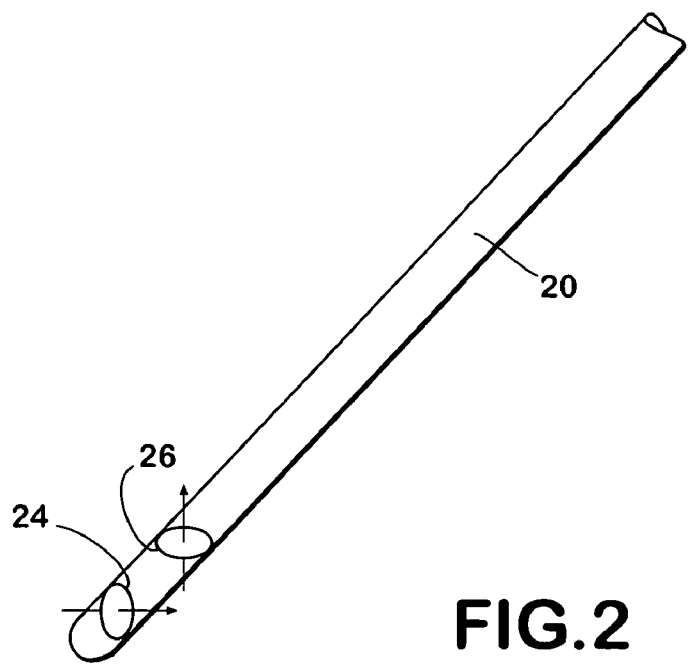
FIG. 2 shows a distal end portion of the probe depicted in the system of FIG. 1.

A system 10 for determining the target point of a drill within a drill bushing is shown in FIG. 1. System 10 is comprised of a probe 12, a handheld guide 14, and a computer 18. As shown in more detail in FIG. 2, probe 12 is comprised of an elongated member 20 to which two drive coils 24, 26 are mounted in orthogonal relationship to one another. The elongated member is typically constructed of main conduit and an integral unit enclosed within a sheath of plastic material with dimensions so that the probe may be inserted in interior passageway 16 of an intramedullary nail 22. Such nails are well-known in the orthopedic field for securing broken bone fragments to one another. The two drive coils may be magnetic dipoles formed by wrapping an electrical conductor around a ferrite core. Preferably, the dipoles are formed by wrapping 201 turns of 44 AWG copper wire around a 1 mm ferrite rod. The drive coils may be fixedly supported within probe 12 or they may be encapsulated within a resin structure joined to the end of a main conduit within probe 12. The most distal drive coil is placed at a position on probe 12 that is proximate a hole 28 through intramedullary nail 22. The drive coils are placed as close as possible to one another so that the magnetic fields generated by the two coils approximately have the same origin with respect to sensor coils located approximately 10 cm or more from the drive coils. Preferably, the two drive coils are separated by a distance of approximately 0.100 inches or less. Drive coils 24 and 26 are oriented in orthogonal relationship so that the fields generated by the coils are orthogonal to one another and to the longitudinal axis of probe 12. This enables computer 18 to determine a target point for an instrument located within drill bushing 40.

Drive coils 24 and 26 may be time multiplexed or frequency multiplexed. Time multiplexing requires that a single alternating current frequency be coupled to only one drive coil at a time. This ensures that when one drive coil generates a magnetic field the other coil is not generating a magnetic field. Generating the magnetic fields with drive coils 24 and 26 so they do not exist at the same time enables the electronics in guide 14 to measure the electrical signals induced in sensors 50*a*, 50*b*, 52*a*, and 52*b* (FIG. 1) without having to adjust for any contribution from the other magnetic field generated by the drive coils. However, for computer 18 to use the readings from guide 14 correctly, the active drive coil must be identified. This active drive coil identification data enables computer 18 to correlate the sensor readings to the terms within the equations used for computing positional data. The active drive coil identification data may be provided by computer 18 to probe 12 so probe 12 provides the alternating current to the corresponding drive coil. When computer 18 sends different active drive coil identification data, probe 12 decouples the active drive coil and couples the drive coil identified by the identification data to the alternating current source. Alternatively, probe 12 may alternate between applying the alternating current to the two drive coils without input from computer 18. In this mode of operation, probe 12 sends active drive coil identification data to computer 18 so computer 18 may correctly correlate the sensor readings it obtains from guide 14 to the active drive coil identified by the identification data from probe 12. Although the active drive coil identification data may be communicated between computer 18 and probe 12 wirelessly or through a communication cable, wireless communication is preferred to obtain the advantages of reduced risk of cable entanglement and to avoid the need of sterilizing cables. To that end, computer 18 and probe 12 are provided with transceivers to support communication between these system components. Preferably, the transceivers conform to the Bluetooth standard. The sending of the active coil identification data is used to synchronize a reference signal that is used for demodulating the responses of the sensors.

The time multiplexed application of the alternating current to the two drive coils uses a preferred current frequency of 25 KHz, although a current frequency within the range of 20 KHz to 30 KHz may be used. A high current frequency is preferred because a higher frequency improves the coupling between an emitted magnetic field and the sensor coils. However, intramedullary nails are typically constructed of metallic materials. As the emitted field frequency increases, eddy currents are produced in the metals in response to the changing magnetic fields and these eddy currents may significantly attenuate the magnetic field strength. This attenuation is related to the thickness and conductivity of the material from which the intramedullary nail is constructed. Typically, intramedullary nails are made from stainless steel or titanium. Drive coils driven with an alternating current source of 25 KHz work well within nails made of these materials, although other current frequencies may be used provided that the attenuation factor is addressed at higher frequencies. Increasing the amplitude of the alternating current source is one way of compensating for attenuation at higher frequencies. Of course, other current frequencies may be used or preferred with intramedullary nails constructed of other metallic materials or having an atypical thickness.

Preferably, drive coils 24 and 26 are each driven simultaneously by a different alternating current frequency. This frequency multiplexed method of operating the drive coils does not require the alternating application of the alternating current to the drive coils discussed above in the time multiplexed method. Rather, by synchronizing and multiplying a signal obtained from a sensor coil with a reference signal corresponding to one of the two currents applied to the drive coils, a sensor reading is demodulated to obtain a measurement of the response of the sensor coil to the magnetic field generated by a particular drive coil. Preferably, a reading from a sensor coil is provided as an input to a pair of demodulation circuits. One demodulation circuit is coupled to a reference signal corresponding to one of the drive coil frequencies and the other demodulation circuit is coupled to the other drive coil frequency. The output of one demodulation circuit provides the sensor response to one magnetic field while the output of the other demodulation circuit provides the sensor response to the other demodulation circuit. A phase locked loop keeps the reference signals in phase with the currents driving the drive coils as described more fully below.

Handheld guide 14 is comprised of a hand grip 30 that may be mounted between an upper platform 34 and a lower platform 38 or hand grip 30 may be integrally formed with the platforms. A drill bushing 40 having an axis 32 extends from upper platform 34 to lower platform 38 to guide the path of scalpels, drill bits, or screwdrivers. Two sensor planes 44 and 48 are placed orthogonal to one another between upper platform 34 and lower platform 38. Each sensor plane contains at least two sensors that are arranged vertically within a sensor plane and the centers of the sensors within a sensor plane are vertically aligned. Furthermore, the center of sensor 50*a* is horizontally aligned with the center of a sensor 52*a*. Sensors 50*a*, 50*b*, 52*a*, and 52*b* are coupled to signal measurement circuitry within guide 14 although the signals could be provided to computer 18 for measurement. The signal measurement circuitry for synchronizing and demodulating the sensor responses may be contained within hand grip 30 or computer 18. Computer 18 may be coupled to guide 14 by a cable or an RF link may be used to communicate between computer 18 and guide 14. Preferably, the RF link is a wireless link meeting the Bluetooth standard. Preferably, the surgeon may decide whether to couple computer 18 to guide 14 by cable or wireless link and computer 18 and guide 14 may be adapted for selective use of either communication method.

Sensor planes 44 and 48 have dimensions of approximately 2 inches by 1 inch and the sensors are spirals that are approximately 1 inch in diameter. Sensors 50 and 52 may be electrical conductors arranged in a spiral pattern or they may be Hall effect or other magnetic field sensors. Sensors 50 and 52 generate electrical signals in response to components of magnetic flux generated by drive coils 24 and 26 that are parallel to the axis of the sensors.

Computer 18 may be a computer system having a Pentium processor or better, 16 MB of RAM, and a 20 GB hard drive. Alternatively, computer 18 may be an application specific integrated circuit (ASIC) with appropriate support circuits for controlling probe 12 and obtaining sensor readings from guide 14. The circuitry for controlling application timing of an alternating current to the drive coils may be located within probe 12. Programmed instructions for the operation of computer 18 may be stored on the hard drive or they may be stored in non-volatile memory such as a PROM or ROM. The programmed instructions enable computer 18 to control the operation of probe 12 and to analyze the data obtained from sensors 50a, 50b, 52a, and 52b through guide 14.

Figure 3:
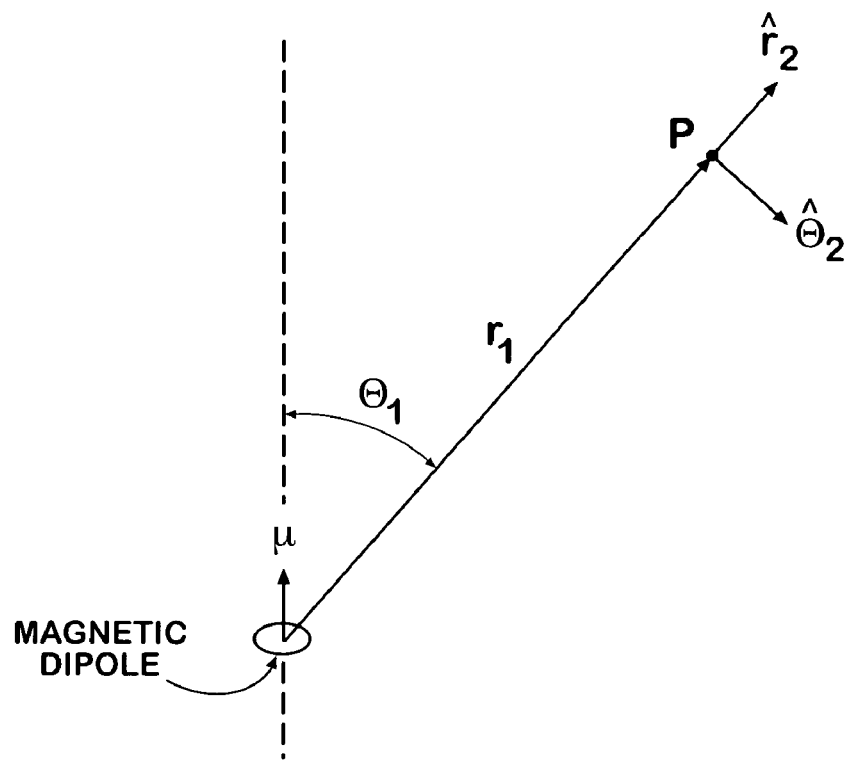
FIG. 3 is a diagram depicting the parameters for determining the magnetic flux density at a point in space.

The magnetic flux density at a point in space may be defined by the equation: $B = \mu_0 \, m / 4\pi r^3 (2 \cos \theta_1 r_2 + \sin \theta_1 \theta_2)$, where B is the magnetic flux density, $\mu_0$ is the magnetic permeability of free space, m is the dipole moment, r is the radial distance from the dipole to the point at which the measurement is being taken, and $\theta_1$ is the angle from the direction of the magnetic field to the point as shown in FIG. 3. Also, $r_2$ and $\theta_2$ represent unit vectors and their angular orientation at the point of measurement. This equation accurately describes the magnetic flux density at a point provided that the radial distance r is substantially larger than the radius of the dipole.

Figure 4:
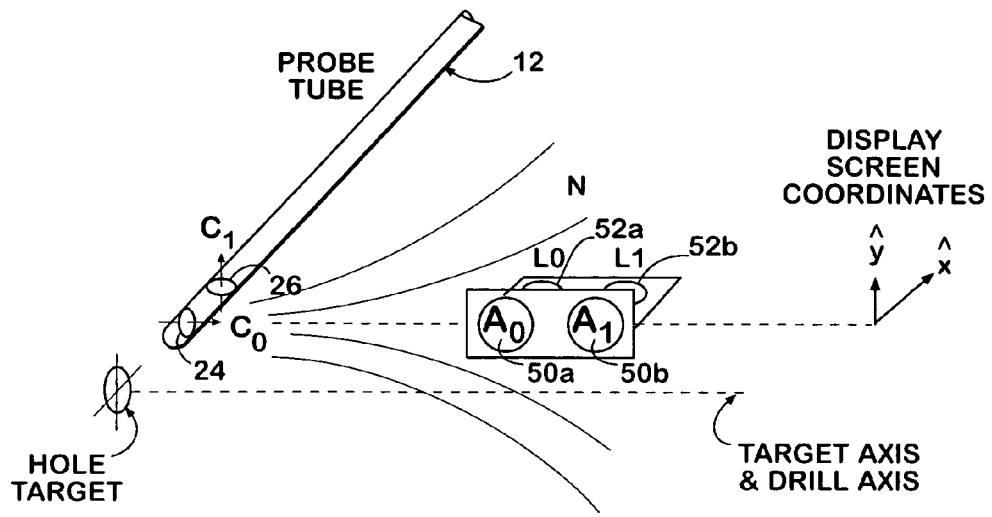
FIG. 4 is a depiction of the relationship between the magnetic tields emitted by the drive coils of FIG. 1 and their interaction with the sensors contained in the sensor planes of FIG. 1.

As shown in FIG. 4, the magnetic field generated by drive coil 24 has a polar orientation that is perpendicular to the axis of probe 12. The magnetic field generated by drive coil 26 has a polar orientation that is perpendicular to the axis of probe 12 and perpendicular to the polar orientation of the field generated by drive coil 24. The magnetic field generated by drive coil 24 induces a current in sensors 50a, 50b, 52a, and 52b and the signal measurement circuitry in guide 14 may be used to obtain a measurement of these currents. Likewise, the magnetic field generated by drive coil 26 induces a current in sensors 50a, 50b, 52a, and 52b and the signal measurement circuitry in guide 14 may be used to obtain a measurement of these currents. Thus, eight measurements may be obtained from the interaction of the sensors with the magnetic fields generated by drive coils 24 and 26. Sensor planes 44 and 48 are arranged orthogonally so that sensor coils 50a, 50b, 52a, and 52b generate responses of zero in response to the field generated by drive coil 24 when axis 32 of drill bushing 40 is aligned with hole 28. This occurs because the constant magnetic flux line of the field generated by drive coil 24 passes through the center of sensor planes 44 and 48. However, the constant magnetic flux line of the field generated by drive coil 26 does not pass through sensor planes 44 and 48 when bushing 40 is aligned with hole 28 so sensors 50a, 50b, 52a, and 52b continue to generate sensor readings during alignment.

Figures 5, 6:
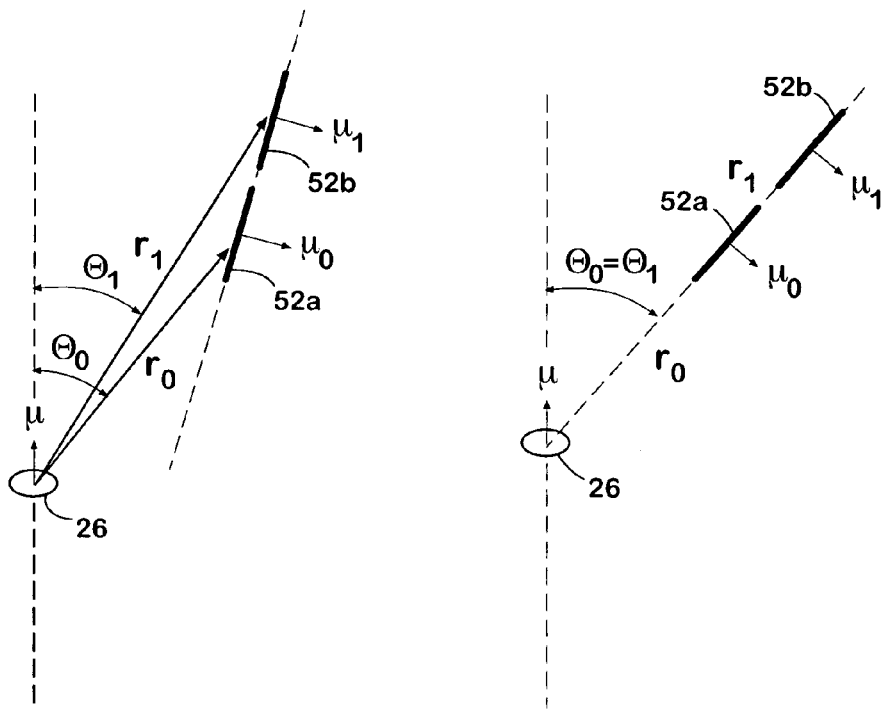
FIG. 5 depicts the relationships between a magnetic dipole and the sensors of a sensor plane when the plane does not point to the dipole.
FIG. 6 depicts the relationships between a magnetic dipole and the sensors of a sensor plane when the plane points to the dipole.

When handheld guide 14 is tilted so that the axis defined by one of the sensor planes 44 or 48 does not intersect the plane in which drive coil 24 is located, as shown in FIG. 5, the centers of the two sensors contained in the sensor plane are at different radial distances and different angles. Thus, the measurements at the two sensors vary by the radial distance of the points to the dipole, as set forth in the equation noted above, as well as by the angular terms of that equation. However, when handheld guide 14 is aligned so it intersects the magnetic dipole as shown in FIG. 6, the sensors are at the same angle from the magnetic axis of the drive coil although the electrical signals generated by the sensors differ as a result of having different radial distances only. That is, the angle $\theta_1$ for both coils are the same and therefore, the $(2 \cos \theta_1 r_2 + \sin \theta_1 \theta_2)$ terms for the two measurements are the same.

With this geometric information regarding the magnetic flux densities at the points represented by the magnetic moments of sensors 50a, 50b, 52a, and 52b, computer 18 may be programmed to determine the offset of the bushing alignment from drive coil 24 so that a target point may be projected as a displaced point on a display or as directional indicia on the handheld guide. For example, a display screen 36 (FIG. 1) that may be associated with computer 18 may be used to display a set of cross-hairs 54 that indicate the position of the targeted hole that is proximate drive coil 24. Target dot 58 provides an indication of the two dimensional displacement of the projected target point extending from the drill bushing to a plane that is orthogonal to the axis of drive coil 24. The position of guide cross 60 indicates the deviation of the axis of the drill bushing from being aligned with the axis of hole 28 proximate drive coil 24. The angular orientation of the crossed lines 62 in guide cross 60 indicates the angular rotation of sensor plane 48 with the magnetic field generated by drive coil 26. While computer 18 may alternatively or additionally generate these indicia for presentation on a display associated with computer 18, computer 18 may generate a target directional signal, an axis alignment signal, and an angular orientation signal that may be used to illuminate directional indicators (not shown) associated with handheld guide 14. The target directional signal may be used to illuminate directional arrows to indicate the direction in which the surgeon should move the forward end of drill bushing to point towards drive coil 24. The axis alignment signal may be used to illuminate directional arrows to indicate the direction in which the surgeon should move guide 14 to align drill bushing 40 with the axis of hole 28 in intramedullary nail 22. The angular orientation signal may be used to illuminate directional arrows to indicate the direction in which guide 14 should be rotated to aligned sensor planes 44 and 48 with the magnetic axis of drive coils 24 and 26.

Once computer 18 has obtained the electrical signal measurements from the four sensors 50a, 50b, 52a, and 52b induced by the magnetic field generated by drive coil 24 (denoted as C0 in FIG. 4) and the electrical signal measurements from the four sensors induced by the magnetic field generated by drive coil 26 (denoted as C1 in FIG. 4), the target symbol position may be computed. Computer 18 may use the following equation to compute the target symbol position: Target position=(Sensor $50b_{C0}$/Sensor $52b_{C1}$−Sensor $50a_{C0}$/Sensor $52a_{C1}$)x+(Sensor $52b_{C0}$/Sensor $52b_{C1}$−Sensor $52a_{C0}$/Sensor $52a_{C1}$)y. The subscripts indicate that the measurement at a particular sensor is taken while the sensor is within the magnetic field generated by the drive coil identified by the subscript. The x and y subscripts denote the directions in each of the display axes. Substitution of the magnetic flux density equation noted above for each sensor reading in the target position equation shows that the position is directly proportional to the measurements because the $\mu m/4\pi$ terms in the denominator and nominator for each sensor reading cancel and the $r^3$ terms for the denominator and nominator are approximately equal so they cancel as well. Preferably, the sensor $52b_{C1}$ reading is replaced by the magnitude of the field produced by drive coil 26 at sensors 50b and 52b while the sensor $52a_{C1}$ reading is replaced by the magnitude of the field produced by drive coil 26 at sensors 50a and 52a. Therefore, if the sensor plane contains the drive coil, the computed target position is zero. The field magnitude for drive coil 26 at sensors 50b and 52b may be described by the equation: $((\text{Sensor } 52b_{C1})^2 + (\text{Sensor } 50b^{C1})^2)^{1/2}$ while the field magnitude for drive coil 26 at sensors 50a and 52a may be described by the equation: $((\text{Sensor } 52a_{C1})^2 + (\text{Sensor } 50a_{C1})^2)^{1/2}$. Use of this field magnitude computation provides an accurate target symbol determination when guide 14 is rotated about the axis of drill bushing 40.

Computer 18 may compute the position for guide cross 60 from the equation: Sensor $50a_{C0}$x+Sensor $52a_{C0}$y. This value may be divided by $((\text{Sensor } 52a_{C1})^2 + (\text{Sensor } 50a^{C1})^2)^{1/2}$ to cancel the $\mu_0 m/4\pi$ terms in the numerator and denominator. The rotation angle of guide cross 60 may be determined from the equation: (Sensor $52a_{C1}$x+Sensor $50a_{C1}$y)/$((\text{Sensor } 52a_{C1})^2 + (\text{Sensor } 50a_{C1})^2)^{1/2}$. Thus, computer 18 may determine the target point for drill bushing 40, the alignment of drill bushing 40 with the axis of hole 28 proximate drive coil 24, and the angular orientation of drill bushing 40 from the electrical signal measurements taken at sensors 50a, 50b, 52a, and 52b that are contained in sensor planes 44 and 48.

Figure 7:
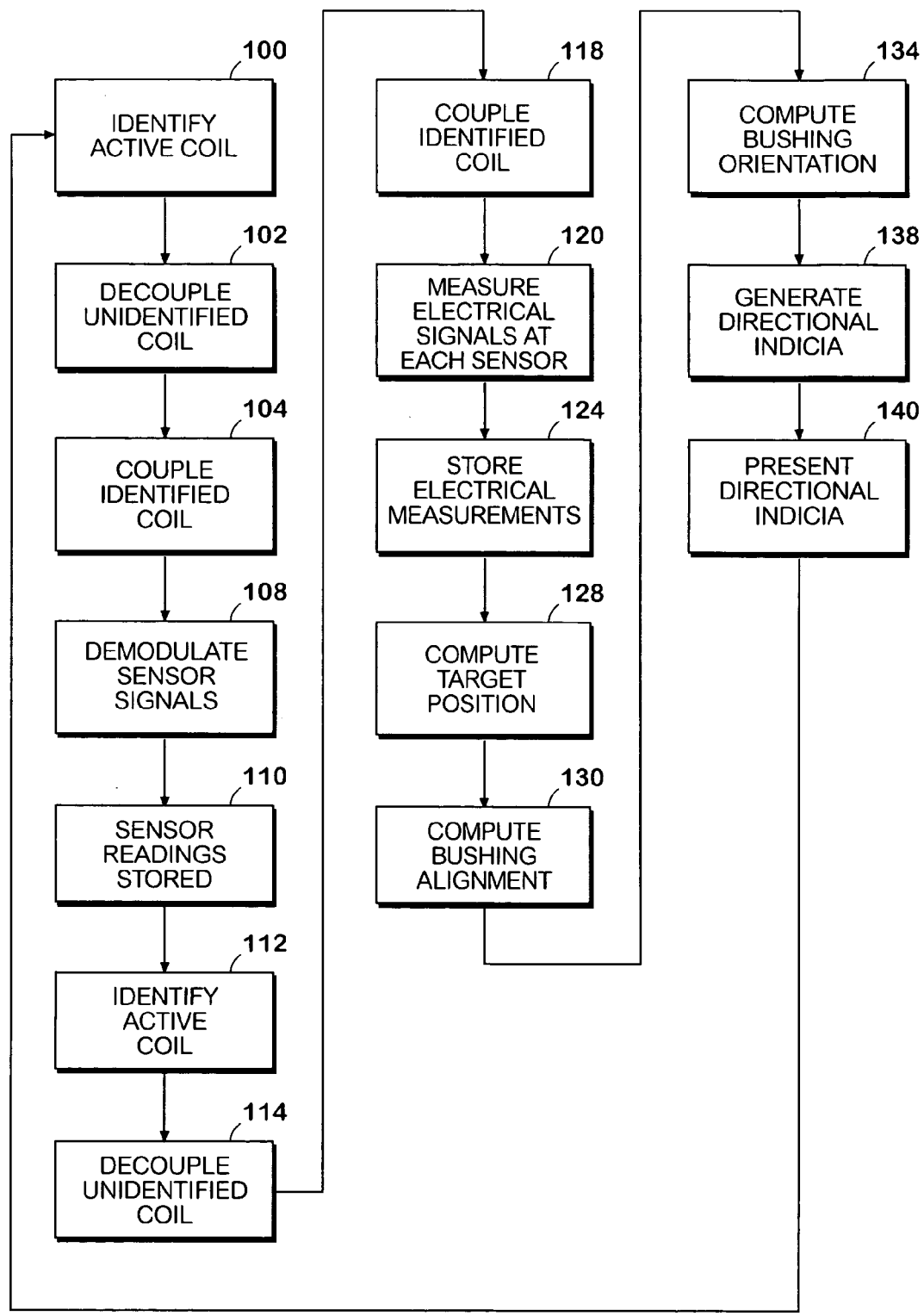
FIG. 7 is a flowchart of an exemplary process for determining the target point, bushing alignment, and bushing orientation that uses a single alternating current frequency.

An exemplary program that operates system 10 in the time multiplexed mode to determine target position, axis alignment, and angular rotation may implement the process shown in FIG. 7. The process begins by identifying an active drive coil (box 100). In response to the identification data, the unidentified drive coil, for example, drive coil 26, is decoupled from the alternating current supply (box 102) while the identified drive coil, in the example, drive coil 24 is coupled to the alternating current (box 104). The signals from each of the sensors in sensor planes 44 and 48 are demodulated (box 108) and these sensor readings are stored in computer memory in association with the active drive coil (box 110). The active drive coil identification data is updated (box 112). The drive coil not identified by the data is decoupled from the alternating current supply (box 114) and the drive coil identified by the data is coupled to the alternating current supply (box 118). The signals from each of the sensors in sensor planes 44 and 48 are demodulated (box 120) and these sensor readings are stored in computer memory in association with the active drive coil (box 124). Target position may now be computed using the equation described above and the eight measurements (box 128). Likewise, drill bushing alignment (box 130) and drill bushing rotation (box 134) may be determined. These values are used to generate indicia (box 138) for presentation on display 50 or, either alternatively or additionally, used to control directional indicia on guide 14. Alternatively, data values from multiple samplings for each sensor may be stored in a buffer and averaged to generate values for substitution into the above described equations. A data value average may be a mean average or weighted average.

Figure 8:
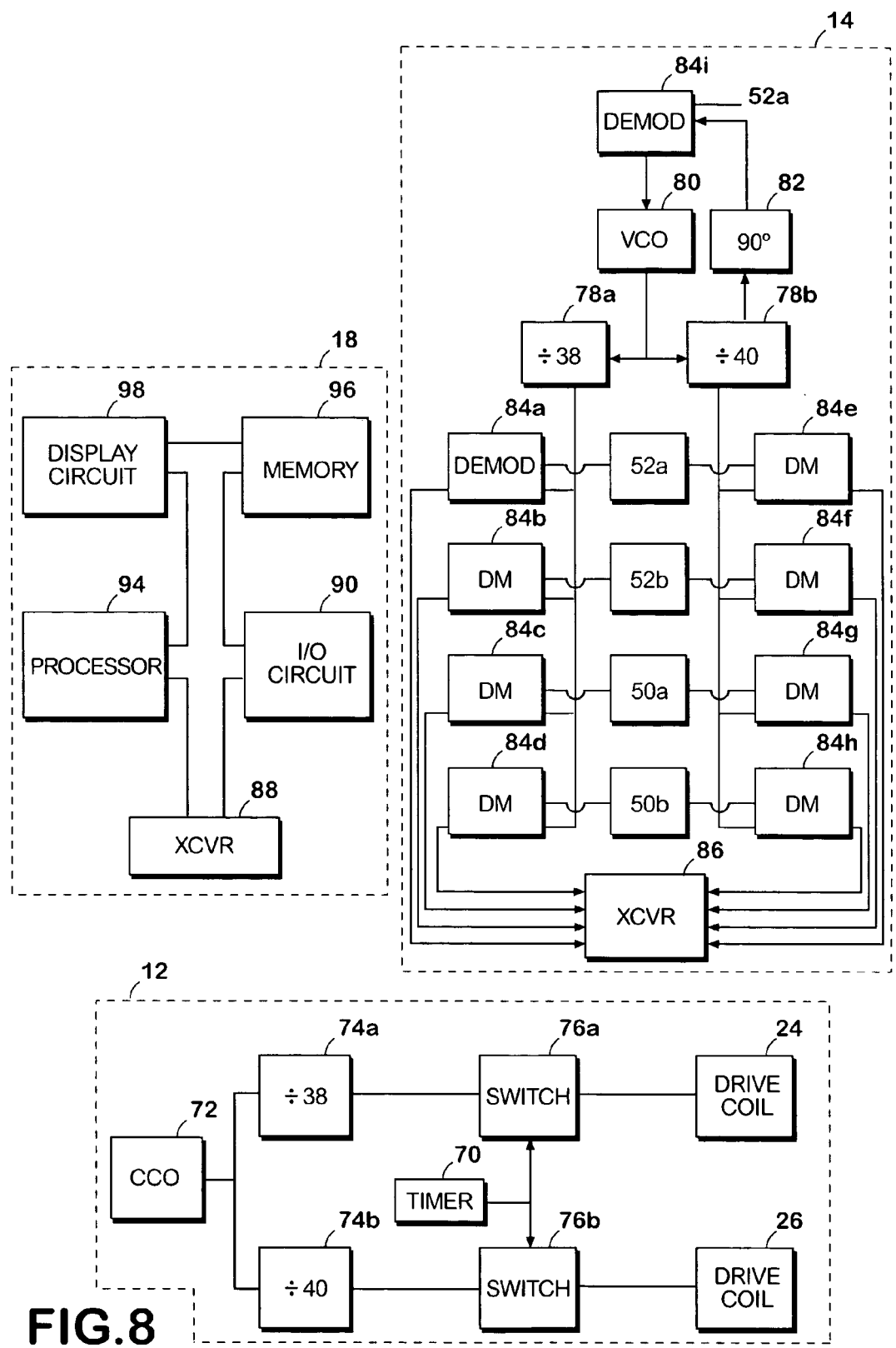
FIG. 8 is a block diagram of an exemplary system for implementing the frequency multiplexed method for determining target point, bushing alignment, and bushing orientation.

Components of system 10 for determining positional data by using a frequency multiplexed method are shown in FIG. 8. System 10 includes computer 18, probe 12, and guide 14. Within probe 12 is a timer 70, a crystal controlled oscillator 72, two dividers 74a, 74b, and switches 76a, 76b. Crystal oscillator 72 is powered by a battery (not shown) so that it free runs to generate an alternating current, which is preferably at a frequency of 1 MHz. Divider 74a, preferably, divides the oscillator signal by 38 while divider 74b, preferably, divides the oscillator signal by 40. Thus, dividers 74a and 74b preferably produce a 26.315 KHz alternating current and a 25.000 KHz alternating current, respectively. Timer 70 enables switches 76a and 76b so they pass the alternating currents to drive coils 24 and 26. Preferably, timer 70 enables switches 76a and 76b to pass the generated alternating currents for 760 μseconds and then disables switches 76a and 76b for 40 μseconds. Thus, the two alternating currents that are applied to drive coils 24 and 26 are closely in phase with one another at the beginning of the signal burst. The circuitry in probe 12 continually runs so that drive coils 24 and 26 generate magnetic fields for 760 μseconds and then turn off for 40 μseconds. Preferably, dividers 74a and 74b and timer 70 are implemented by a microprocessor executing software although they may be implemented by known counters and discrete logic components.

Within guide 14 are eight demodulation circuits 84a, 84b, 84c, 84d, 84e, 84f, 84g, and 84h. Demodulation circuit 84i is used for phase synchronization as explained below. VCO 80 generates an alternating current that is divided by dividers 78a and 78b. The frequency generated by VCO 80 and dividers 78a and 78b are adjusted so that the two alternating currents generated from dividers 78a and 78b are the same frequency as the two currents applied to drive coils 24 and 26 in probe 12. Thus, VCO 80 preferably generates a 1 MHz signal and dividers 78a and 78b are preferably divide by 38 and divide by 40 frequency dividers, respectively, to generate signals having a frequency of 26.315 KHz and 25.000 KHz. The signal from divider 78a is provided as a reference signal to demodulation circuits 84a, 84b, 84c, and 84d while the signal from divider 78b is applied as a reference signal to demodulation circuits 84e, 84f, 84g, 84h. The response signal from sensor 52a is coupled to demodulation circuits 84a and 84e, sensor 52b is coupled to demodulation circuits 84b and 84f, sensor 50a is coupled to demodulation circuits 84c and 84g, and sensor 50b is coupled to demodulation circuits 84d and 84h. Thus, each sensor is coupled to a pair of demodulation circuits and one demodulation circuit is coupled to a reference signal that corresponds to the drive current for generating one magnetic field produced by probe 12 while the other demodulation circuit is coupled to a reference signal that corresponds to the drive current generating the other magnetic field produced by probe 12. The demodulation circuits 84a–84h average the product of the reference signal and the sensor reading signal while the magnetic fields are being generated by probe 12. The values from each demodulation circuit 84a–84h are provided to transceiver 86 for transmission to transceiver 88 in computer 18. Preferably, transceivers 86 and 88 communicate in conformance with the Bluetooth standard. Alternatively, the values may be provided to I/O circuitry for delivery to computer 18 by conductors in a cable. Preferably, computer 18 and guide 14 are configured for communicating with one another both wirelessly and through wired components so a surgeon may determine the mode of communication to be used during a surgery. Thus, system 10 may be operated without cables between computer 18 and either probe 12 or guide 14. The mode of operation reduces the need for sterilized cables as well as the likelihood of entanglement with other cables in the operating room.

The reference signals generated by dividers 78a and 78b are synchronized with the reference signals applied to drive coils 24 and 26 by the operation of VCO 80, phase shifter 82, and demodulation circuit 84i. Because the field generated by drive coil 26 always cuts the sensors in sensor planes 44 and 48, the reference signal corresponding to the current applied to drive coil 26 is applied to phase shifter 90. Phase shifter 90 shifts the phase of the reference signal by 90° and provides it as an input to demodulation circuit 84i. The signal induced in sensor 52a is preferably selected for input to demodulation signal 84i because it is closer to drive coil 26 although other sensor signals may be used. The sensor closest to a drive coil is cut by flux lines having a greater magnitude. The average product generated by demodulation circuit 84i is centered about zero because two signals at the same frequency that are exactly 90° out of phase generate a product of zero. As the output of demodulation circuit 84i goes above or below zero, it alters the operation of VCO 80 to shift the frequency of the signal generated by VCO 80 so it synchronizes with the current being applied to drive coil 26. Separate synchronization for the reference signal applied to drive coil 24 is not required, although it could be achieved in a similar manner, because the currents applied to drive coils 24 and 26 are closely synchronized as both are derived from the same clock signal in probe 12. The phases of the currents applied to drive coils 24 and 26 at the beginning of the burst are known to be in-phase. By detecting the 40

μsecond period of inactivity at the phase locked loop, the phase of drive coil 24 is known to be synchronized with the phase of drive coil 26 detected at the phase locked loop. This is important because the signal from drive coil 24 approaches zero as guide 14 is aligned with targeted hole 28 in nail 22.

Computer 18 includes input/output (I/O) circuitry 90 for communication with guide 14. Computer 18 also includes a processor 94, memory 96, and display circuit 98. Processor 94 executes instructions to control the operation of system 10. The data received from guide 14 is stored in memory 96 and the positional data computed by processor 94 is provided to display circuit 98 for presentation to the surgeon.

Figure 9:
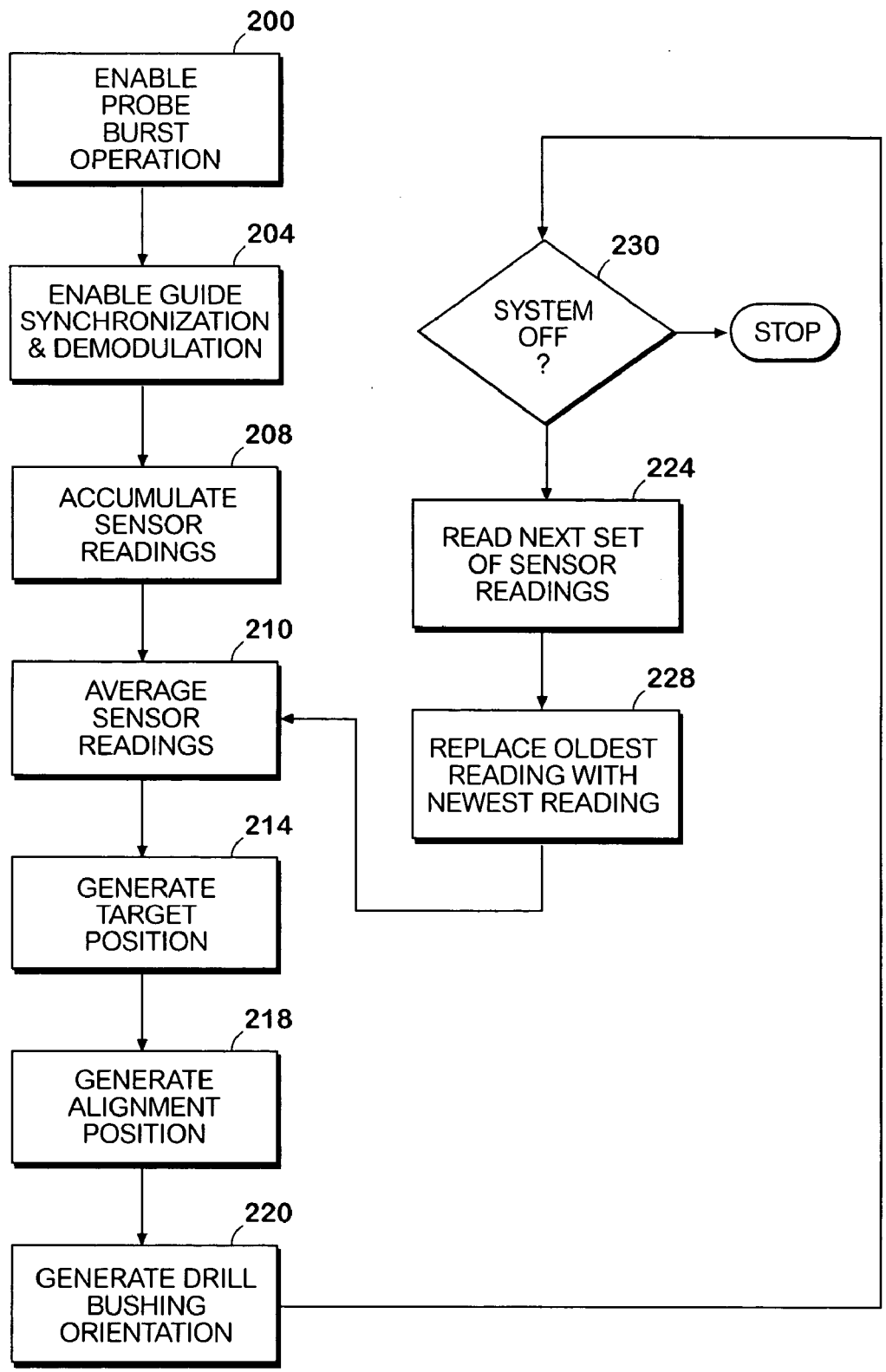
FIG. 9 is a flowchart of an exemplary process for determining target point, bushing alignment, and bushing orientation using the frequency multiplexed method.

An exemplary process for operating system 10 in the frequency multiplexed mode to determine target position, axis alignment, and angular rotation is shown in FIG. 9. The process begins by enabling probe 12 current to begin its burst mode of operation for stimulating drive coils 24 and 26 (box 200). Preferably, the probe current circuitry applies an alternating current having a frequency of 26.315 KHz to drive coil 24 and an alternating current having a frequency of 25.000 KHz to drive coil 26 for 760 μseconds. The circuitry then turns off the alternating currents to both drive coils for 40 μseconds. The two alternating current frequencies are chosen to provide an integral number of complete cycles during the burst period. The turn off period is provided so a signal from the phase locked loop for drive coil 26 in guide 14 may be used to determine the phase of the signal driving drive coil 24. Because the magnetic field from drive coil 24 does not cause the sensors to generate a reading at the aligned position, its phase cannot be determined at the aligned position. However, the phase of the signal driving drive coil 26 may be determined by the phase locked loop for drive coil 26 in guide 14 because the magnetic field emitted by drive coil 26 causes signals in the sensors at the aligned position. The turn off period then enables the demodulation circuitry for drive coil 24 to detect the start of the burst period. At that time, the phase of the alternating currents for both drive coils is the same because the burst period begins with zero shift between the two currents applied to the drive coils. Thus, the demodulation circuitry for drive coil 24 is able to resynchronize every 800 microseconds at the phase alignment condition.

The process continues by enabling guide 14 to read the sensors in the sensor planes, to synchronize its reference signals with the driving currents in probe 12, and to demodulate the sensor readings (box 204). Thereafter, this circuitry obtains a reading from each sensor 50a, 50b, 52a, and 52b during the 760 μsecond period and demodulates the readings by averaging the product of a reference signal and a sensor reading as explained above. An in-phase relationship between the reference signal and the sensor reading signal is maintained by a phase lock loop circuit. Data corresponding to the demodulated signal are captured and provided to computer 18.

Once the drive coil control circuit (box 200) and the sensor reading circuits (box 204) have been enabled, the process obtains sensor readings from guide 14 (box 208). These readings are accumulated in memory within computer 18 to form an average. Preferably, 125 readings for each sensor are averaged before computer 18 begins solving the position equations. The number of readings (125) multiplied by the period of time for obtaining one reading (800 μseconds) yields a time period of 0.10 seconds and that period corresponds to a frequency of 10 Hz. That frequency is a sub-multiple of the 50 or 60 Hz frequency at which power is supplied in most developed countries having a power grid. By selecting a sub-multiple of both 50 Hz and 60 Hz, the system does not need to be modified or adjusted for use in countries delivering power at either frequency.

The process averages the readings to generate a sensor value (box 210). These values are used to generate the target position (box 214), the alignment position (box 218), and the drill bushing orientation (box 220) using the equations noted above. Upon acquisition of the next set of sensor readings (box 224), the oldest reading value is replaced with the most recent sensor reading (box 224). The readings are averaged (box 210) and the position values are determined using the updated values (boxes 214, 218, and 220). This process of replacing the oldest stored sensor value with the most recent one, updating the sensor values, and re-computing the position values continues until computer 18 is reset or turned off (box 230).

Figure 10:
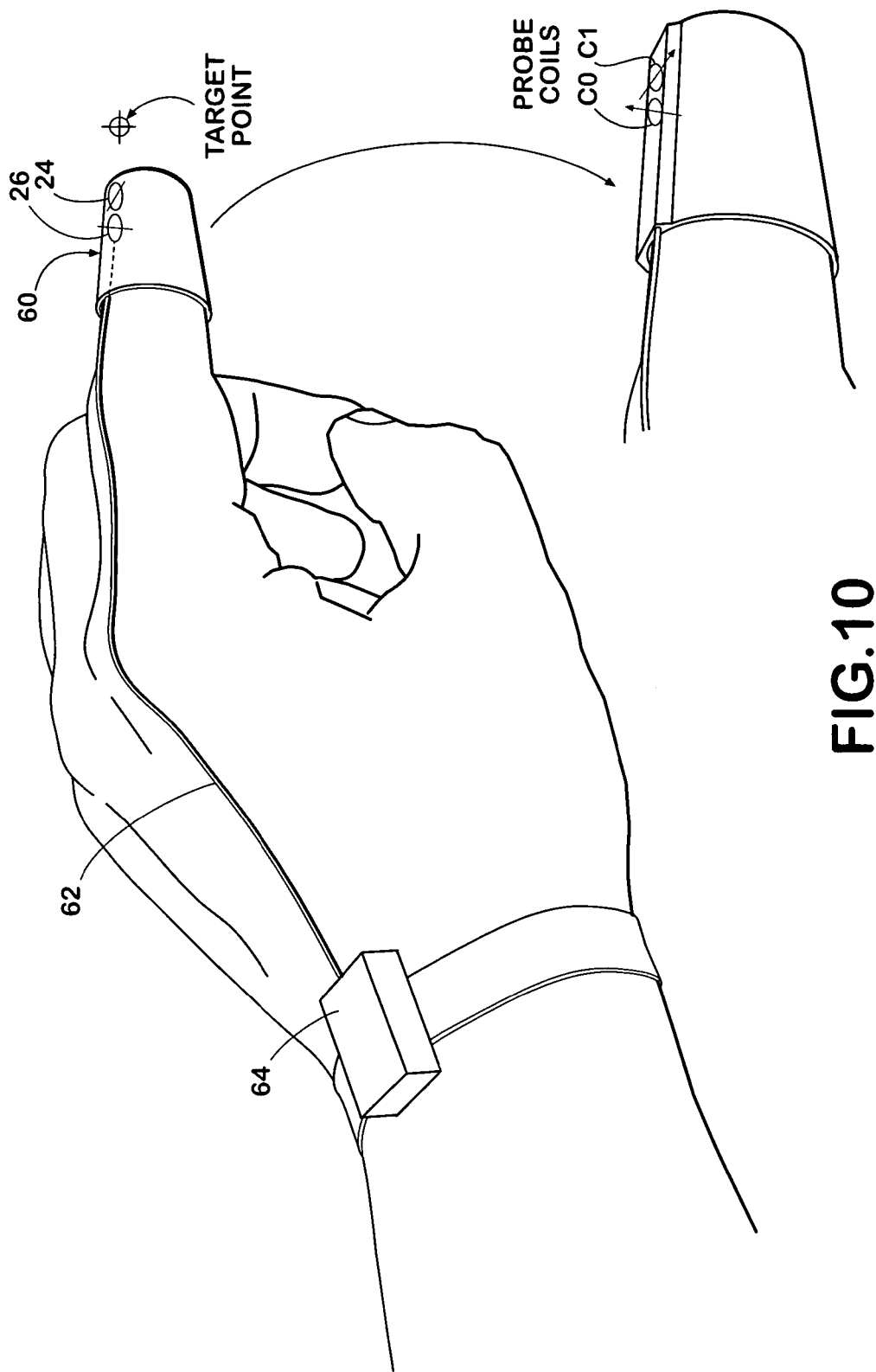
FIG. 10 depicts an alternative embodiment of the probe shown in FIG. 1 in which the drive coils are mounted within a glove or thimble.

In another alternative embodiment of the present invention shown in FIG. 10, two drive coils 24, 26 may be embedded or otherwise placed within an elastic material that is formed in a thimble 60 for placement on a surgeon's finger or in a glove for encasing a surgeon's hand. Preferably, drive coils 24, 26 are located at the distal end of a finger or thumb as shown in the thimble embodiment. The drive coils are separated by approximately 0.100 inches or less along the longitudinal axis of a finger, thumb, or thimble. Electrical leads 62 from drive coils 24, 26 may be used to couple the drive coils to circuitry such as that shown in FIG. 8 for probe 12 for frequency multiplexed operation of the drive coils. Alternatively, the drive coils may be coupled in an alternating manner to a single alternating current frequency in the time multiplexed operation discussed above. Once the drive coils are coupled to a driving current, the surgeon may place the digit bearing thimble 60 so that drive coils 24, 26 are proximate a point at which the surgeon desires a surgical instrument to exit. By placing the drill bushing at the selected entrance site, the surgeon may then observe the effects of altering the angular orientation of the drill bushing on the displayed target point. Once the target point is centered in cross-hairs 54, the surgeon knows that drilling will proceed from the entrance point to the point proximate drive coil 24. The surgeon may continue to observe the target point projection of drill bushing 40 until the surgeon begins to feel the protuberance of the drill at drive coil 24. In this manner, a surgeon may perform point-to-point drilling using the glove or thimble embodiment. Of course, drive coils 24, 26 may be incorporated in other structures to facilitate placement of the drive coils at an exit point for such drilling.

While the present invention has been illustrated by the description of exemplary processes and system components, and while the various processes and components have been described in considerable detail, applicant does not intend to restrict or in any limit the scope of the appended claims to such detail. Additional advantages and modifications will also readily appear to those skilled in the art. For example, the system of the present invention has been described as having two drive coils in its probe and sensor coils associated with the guide. However, this arrangement may be reversed with the drive coils mounted orthogonal to one another and in close proximate relationship at the guide while the sensor coils are orthogonally arranged in the probe. Likewise, the invention has been described as using two drive coils and four sensors but more sensors may be used for additional refinement of the position calculations. Therefore, the invention in its broadest aspects is not limited to the specific details, implementations, or illustrative examples shown and described. Accordingly, departures may be made from such details without departing from the spirit or scope of applicant's general inventive concept.

What is claimed is:

1. A system for locating a target point for a drill bushing comprising:
   a probe having two drive coils, the drive coils being mounted in the probe and being oriented so that a magnetic field produced by the first drive coil in response to an alternating current being coupled to the first drive coil is orthogonal to a magnetic field produced by the second drive coil in response to an alternating current being coupled to the second drive coil;
   a guide having a pair of sensor planes mounted proximate a drill bushing, the sensor planes being orthogonal to one another, each sensor plane containing a pair of sensors, each sensor generating an electrical signal in response to magnetic fields produced by the first and the second drive coils; and
   a computer coupled to the sensors in each sensor plane to receive signal readings from each sensor and to determine the target point of the drill bushing to which the pair of sensor planes is mounted.

2. The system of claim 1 wherein the first and second drive coils are driven by an alternating current of in the range of approximately 20 KHz to 30 KHz to generate magnetic fields.

3. The system of claim 1 wherein the first drive coil is driven by an alternating current of approximately 26.315 KHz to generate magnetic fields and the second drive coil is driven by an alternating current of approximately 25 KHz to generate magnetic fields.

4. The system of claim 1 wherein the sensors in each sensor plane are inductive coil sensors.

5. The system of claim 1 wherein the sensors in each sensor plane are Hall effect sensors.

6. The system of claim 1 wherein the sensors in each sensor plane are magnetoresistive sensors.

7. The system of claim 1 wherein the computer determines alignment of the drill bushing with an axis of an intramedullary nail hole that is proximate one of the drive coils.

8. The system of claim 1 wherein the computer generates target indicia for identifying the target point of the drill bushing in the plane of one of the drive coils.

9. The system of claim 1 wherein the computer generates alignment indicia for identifying alignment of the drill bushing an axis for an intramedullary nail hole that is proximate one of the drive coils.

10. The system of claim 1 wherein the computer generates rotation indicia for identifying an angular orientation of the drill bushing to an intramedullary hole that is proximate one of the drive coils.

11. The system of claim 1 further comprising:
    a display for presentation of indicia indicative of the drill bushing target point.

12. The system of claim 1, the probe further comprising:
    an alternating current source for coupling to the first and the second drive coils; and
    a switch for selectively coupling the alternating current to one or the other drive coil.

13. The system of claim 1 further comprising:
    a first alternating current source for coupling to the first drive coil; and
    a second alternating current source for coupling to the second drive coil.

14. The system of claim 13, the probe further comprising:
    a first switch for selectively coupling the first alternating current to the first drive coil; and
    a second switch for selectively coupling the second alternating current to the second drive coil.

15. The system of claim 14 wherein the first and the second switches selectively couple the first and the second alternating currents to the first and the second drive coils for 760 μseconds.

16. The system of claim 15 wherein the first and the second switches selectively decouple the first and the second alternating currents from the first and the second drive coils for 40 μseconds.

17. The system of claim 13 wherein the first alternating current source is comprised of a clock signal generator and a first divider for generating the first alternating current from the clock signal generated by the clock signal generator; and
    the second alternating current source includes a second divider for generating the second alternating current from the clock signal generated by the clock signal generator so that the relationship of the first and the second alternating currents are closely synchronized.

18. The system of claim 1, the guide further comprising:
    a plurality of demodulation circuits for determining a reading for each sensor's response to a magnetic field generated by one of the drive coils.

19. The system of claim 18, the guide further comprising:
    a phase locked loop for synchronizing a first reference signal to a signal from one of the sensors in a sensor plane.

20. The system of claim 19 wherein the phase locked loop synchronizes the first reference signal to a sensor signal by using the first reference signal shifted by 90°.

21. The system of claim 19 wherein a signal from the phase locked loop control generates first and second reference signals so that the first and second reference signals are substantially in phase with first and second alternating currents being applied to the first and second drive coils.

22. The system of claim 21 wherein the phase of the second reference signal is synchronized with the phase of the first reference signal at the beginning of a burst period.

23. The system of claim 21 wherein the demodulation circuits average the product of one of a first and a second reference signal with a signal from a sensor in a sensor plane to generate a sensor reading.

24. The system of claim 23 wherein the computer averages a plurality of sensor readings for each sensor before determining the target point.

25. The system of claim 24 wherein the computer averages a number of readings that corresponds to a sub-multiple of a power main frequency.

26. The system of claim 25 wherein the computer averages a number of readings that corresponds to a sub-multiple of a 50 Hz and a 60 Hz power main frequency.

27. The system of claim 1, the computer further comprising:
    a transceiver; and
    the guide further comprising a transceiver so that the computer may receive the sensor readings wirelessly from the guide.

28. The system of claim 1 wherein the computer generates active drive coil identification data for identifying one of the first and the second drive coils that is being coupled to the alternating current source.

29. The system of claim 28, the computer further comprising:
   a transmitter for sending the generated active drive coil identification data to the probe; and
   the probe further comprising a receiver for receiving the generated identification data from the computer.

30. The system of claim 28, the probe further comprising:
   a transmitter for sending the generated active drive coil identification data to the computer; and
   the computer further comprising a receiver for receiving the generated identification data from the probe.

31. The system of claim 1 wherein the probe generates active drive coil identification data for identifying one of the first and the second drive coils that is being coupled to the alternating current source.

* * * * *